United States Patent
Van De Wijdeven

(10) Patent No.: US 8,383,134 B2
(45) Date of Patent: *Feb. 26, 2013

(54) BIODEGRADABLE MATERIAL BASED ON OPENED STARCH

(75) Inventor: Gijsbertus Gerardus Petrus Van De Wijdeven, Maastricht (NL)

(73) Assignee: Bioneedle Technologies Group B.V., Eindhoven (NL)

( * ) Notice: Subject to any disclaimer, the term of this patent is extended or adjusted under 35 U.S.C. 154(b) by 494 days.

This patent is subject to a terminal disclaimer.

(21) Appl. No.: 12/529,526

(22) PCT Filed: Feb. 29, 2008

(86) PCT No.: PCT/NL2008/050120
§ 371 (c)(1), (2), (4) Date: Sep. 1, 2009

(87) PCT Pub. No.: WO2008/105662
PCT Pub. Date: Sep. 4, 2008

(65) Prior Publication Data
US 2010/0015185 A1     Jan. 21, 2010

Related U.S. Application Data

(60) Provisional application No. 60/892,416, filed on Mar. 1, 2007.

(30) Foreign Application Priority Data

Mar. 1, 2007  (EP) ..................... 07103338

(51) Int. Cl.
*A61K 9/00* (2006.01)
*A61K 47/00* (2006.01)
*A61F 2/00* (2006.01)
*C08L 3/00* (2006.01)
*C08B 31/00* (2006.01)
*B29C 47/00* (2006.01)
*B29B 7/00* (2006.01)

(52) U.S. Cl. ............... 424/400; 424/426; 264/328.1; 264/323; 514/778; 536/102; 524/47

(58) Field of Classification Search ............... 424/400, 424/426; 514/778; 524/47; 536/102; 264/323, 264/328.1
See application file for complete search history.

(56) References Cited

U.S. PATENT DOCUMENTS

| | | |
|---|---|---|
| 2,668,162 A | 2/1954 | Lowe |
| 3,616,758 A | 11/1971 | Komarov |
| 3,636,956 A | 1/1972 | Schneider |
| 3,839,297 A | 10/1974 | Wasserman et al. |
| 3,982,536 A | 9/1976 | Krogseng et al. |
| 4,137,921 A | 2/1979 | Okuzumi et al. |
| 4,157,437 A | 6/1979 | Okuzumi et al. |
| 4,243,775 A | 1/1981 | Rosensaft et al. |
| 4,443,430 A | 4/1984 | Mattei et al. |
| 4,975,479 A * | 12/1990 | Satake et al. .................. 524/100 |
| 5,076,983 A | 12/1991 | Loomis et al. |
| 5,310,865 A | 5/1994 | Enomoto et al. |
| 5,409,973 A | 4/1995 | Bastioli et al. |
| 5,439,953 A | 8/1995 | Ritter et al. |
| 5,549,560 A | 8/1996 | Van De Wijdeven |
| 5,736,209 A * | 4/1998 | Andersen et al. ............ 428/36.4 |
| 5,989,214 A | 11/1999 | Van De Wijdeven |
| 6,025,458 A | 2/2000 | Lipinsky et al. |
| 6,821,538 B2 | 11/2004 | Axelrod et al. |
| 2010/0080839 A1 * | 4/2010 | Van De Wijdeven ......... 424/426 |

FOREIGN PATENT DOCUMENTS

| | | |
|---|---|---|
| DE | 4038732 A1 | 6/1992 |
| EP | 0118240 A2 | 9/1984 |
| EP | 326517 A1 * | 8/1989 |
| EP | 0522358 A2 | 6/1992 |
| EP | 0298920 B1 | 12/1992 |
| EP | 0560014 A1 | 1/1993 |
| EP | 0400532 B1 | 1/1994 |
| EP | 0282451 B1 | 6/1994 |
| EP | 0437561 B1 | 7/1994 |
| EP | 0544234 B1 | 2/1995 |
| EP | 0494287 B1 | 10/1995 |
| EP | 0679172 A | 11/1995 |
| EP | 0413798 B1 | 12/1995 |
| EP | 0495056 B1 | 12/1995 |
| EP | 0376201 B1 | 6/1996 |
| EP | 0437589 B1 | 7/1996 |
| EP | 0474705 B1 | 8/1996 |
| EP | 0670683 B1 | 9/1996 |
| EP | 0436698 B1 | 11/1996 |
| EP | 0539541 B1 | 7/1997 |

(Continued)

OTHER PUBLICATIONS

Tester et al., International Journal of Biological Macromolecules, 2000, 27, 1-12.*

(Continued)

*Primary Examiner* — Abigail Fisher
(74) *Attorney, Agent, or Firm* — Gilberto M. Villacorta; Sunit Talapatra; Foley & Lardner LLP

(57) ABSTRACT

The present application relates to a biodegradable material comprising opened starch or a mixture of opened starch and destructurised starch. The biodegradable material comprises about 50 to about 100 wt. % of opened starch or of a mixture of opened starch and destructurized starch, based on the total weight of the biodegradable material, said biodegradable material having a bulk density of 1.0 to 1.5 kg/dm. The biodegradable material is used for manufacturing biodegradable shaped articles, wherein said biodegradable shaped articles are suitable for delivery of a biologically or pharmaceutically active component in or to a vertebrate, e.g. a mammal.

28 Claims, 1 Drawing Sheet

FOREIGN PATENT DOCUMENTS

| | | | |
|---|---|---|---|
| EP | 0560244 | B1 | 4/1998 |
| EP | 0519367 | B1 | 9/1998 |
| EP | 0819117 | B1 | 5/1999 |
| EP | 0775171 | B1 | 10/1999 |
| EP | 0682070 | B1 | 1/2000 |
| EP | 1035163 | A2 | 9/2000 |
| EP | 0304401 | B2 | 11/2000 |
| EP | 0327505 | B2 | 11/2001 |
| EP | 0712883 | B1 | 3/2002 |
| EP | 1064330 | B1 | 9/2002 |
| EP | 0711326 | B1 | 10/2002 |
| EP | 0774975 | B1 | 3/2003 |
| EP | 0994654 | B1 | 4/2003 |
| EP | 0575349 | B2 | 8/2003 |
| EP | 1103254 | B1 | 3/2005 |
| EP | 1282662 | B1 | 6/2005 |
| GB | 2190093 | A | 11/1987 |
| NL | 9401372 | A | 4/1996 |

OTHER PUBLICATIONS

Roger et al., Carbohydrate Polymers, 1993, 21, 83-89.*
Zobel, Starch, 1988, 40 (2), 44-50.*
Molecular Mass, obtained online at: http://en.wikipedia.org/wiki/Molecular Mass, downloaded on Jul. 6, 2012.*
Kirk-Othmer, Encyclopedia of Chemical Technology, "Silicon Compounds to Succinic Acid and Succinic Anhydride", Fourth Edition, vol. 22, 1997, pp. 699-719.
International Search Report corresponding to PCT/NL2008/050120, dated May 23, 2008, 3 pages.
Tester et al., "Hydrolysis of native starches with amylases," Animal Feed and Technology, vol. 130, No. 1-2, Sep. 2006, pp. 39-54 [XP005629001].
Van de Wijdeven, "Development and assessment of mini projectiles as drug carriers", Journal of Controlled Release, 85 (2002), pp. 145-162.

* cited by examiner

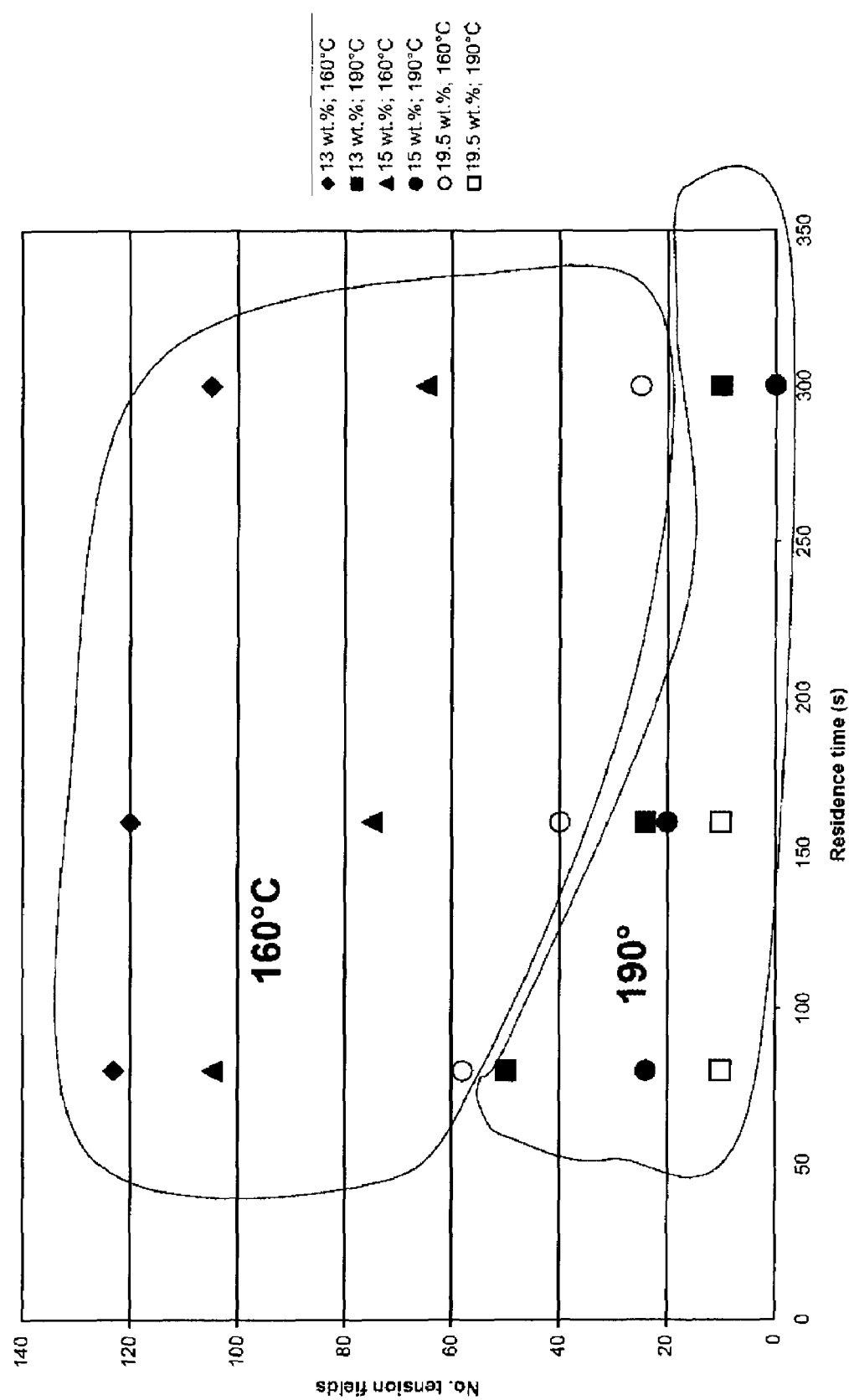

BIODEGRADABLE MATERIAL BASED ON OPENED STARCH

FIELD OF THE INVENTION

The present invention relates to a biodegradable material comprising starch of a particular physical state. The biodegradable material is an excellent starting material for manufacturing biodegradable shaped articles, for example by injection moulding, wherein said biodegradable shaped articles are suitable for delivery of a biologically or pharmaceutically active component in or to a vertebrate, e.g. a mammal. The biodegradable material has a low cytotoxicity. Additionally, the biodegradable shaped articles manufactured from the biodegradable material have excellent tensile strength and bending strength properties. The biodegradable shaped articles are in particular suitable for parenteral, oral, transdermal, subcutaneous and hypodermic applications. In particular, the term "opened starch" relates to a different physical state of the starch than the term "destructurised starch" as used in the prior art dealing with injection mouldable starch compositions. The biodegradability relates to a very fast degradation; fast degradation is a desirable effect for the present invention, whereas for many other applications, fast degradation is not desirable in e.g. blow moulded bottles which must retain their integrity for longer periods of time.

BACKGROUND OF THE INVENTION

Biodegradable materials based on native starch, (chemically) modified starch and like substances are already known in the art for a long period of time.

For example, EP A 118.240 to Warner Lambert Co., incorporated by reference herein, discloses a process for the preparation of a mouldable starch composition, wherein a starch having a molecular weight of 10,000 to 20,000,000 Dalton and a water content of 5 to 30 wt. %, based on the weight of the dry composition, is formulated. The mouldable starch composition is used for the manufacture of injection moulded products, in particular capsules. In the first step of this process, starch is extruded and melted at a temperature of 80° to 240° C. and at a pressure of 60 to 300 MPa ($6 \times 10^7$ to $3 \times 10^8$ $N/m^2$=600 to 3000 bar). In the second step of the process, the melted starch is dissolved in water at a temperature of 80° to 240° C. and at a pressure of 60 to 300 MPa. In the third step of the process, the dissolved starch is plasticized under conditions as employed in the previous step, i.e. at a temperature of 80° to 240° C. and at a pressure of 60 to 300 MPa. Optionally, the starch is mixed with a modified starch. Also optionally, the starch is mixed with additives such as a plasticizer, e.g. polyethylene glycol or glycerol, a lubricant, e.g. a lipid or a phospholipid, or an extender, e.g. gelatine. The injection moulded products, e.g. capsules, are manufactured in the fourth step of the process, wherein the plasticized starch is injected into a mould at a temperature of at least 80° C. and at a pressure of 60 to 300 MPa and a clamping force of 100 to 10,000 kN. However, mechanical properties of the injection moulded products, e.g. the capsules, are not disclosed. Furthermore, cytotoxicity and in vivo degradability properties of the mouldable starch composition are not disclosed. Additionally, as appears from later prior art, the mouldable starch composition can be characterised by the term "destructurised starch" since it is produced from starch that is subjected to a heat treatment that heats the starch to a temperature above its glass transition and melting temperatures with the result that the molecular structure of the starch is at least disordered.

EP A 282.451 of Warner Lambert Co., incorporated by reference herein, also discloses a process for the preparation of a destructurised starch, wherein the starch comprising 10-25 wt. % of water, calculated on the weight of the starch, is further mixed with an inorganic acid, e.g. HCl or $H_2SO_4$. The inorganic acid functions as a chain scission catalysts, i.e. as an agent for acidic hydrolysis, and induces breaking of α-1,4-glycosidic bonds so that a destructurised starch having a decreased molecular weight is formed, i.e. that the average molar mass of the starch is reduced by a factor of 2 to 5,000, preferably 4 to 1,000, more preferably 5 to 300. The process can conveniently be performed in an extruder at a temperature of 100° to 200° C., preferably 140° to 190° C. and most preferably 160° to 185° C. and at relatively low pressures, i.e. a pressure of 0 to 15 MPa (0 to $150 \times 10^5$ $N/m^2$=0 to 150 bar), preferably 0 to 7.5 MPa and most preferably 0 to 5 MPa. The starch may be mixed with additives such as plasticizers, lubricants, extenders and the like, wherein the lubricants may be added without plasticizer or extender. Preferred lubricants are hydrogenated or hardened vegetable or animal fats, optionally in combination with mono- or diglycerides or phosphatides such as lecithin. The destructurised starch can be used to manufacture a range of shaped articles by a range of techniques. For example, thicker walled articles can be made by injection moulding the destructurised starch at a pressure of 30 to 300 MPa, preferably 70 to 220 MPa. The destructurised starch according to EP A 282.451 would be advantageous as it exhibits improved flow characteristics and improved processability which enables lower temperatures and lower pressures to be used in the injection moulding process. However, it is to be expected that shaped articles manufactured from the destructurised starch according to EP A 282.451 have a low tensile strength due to the fact that the destructurised starch has a relatively low molecular weight.

Other processes for the preparation of destructurised starch which is used for the manufacture of shaped articles are for example disclosed in EP A 298.920, GB A 2.190.093, EP A 304.401, EP A 474.705, EP 495.056, EP A 774.975 and EP A 994.564, all incorporated by reference herein.

U.S. Pat. No. 5,409,973, incorporated by reference, also discloses a process for the preparation of destructurised starch, wherein starch is extruded in the presence of up to 20 wt. % of water (this amount included the intrinsic water content of the starch employed), based on the total weight of the composition supplied to the extruder, wherein the water content is reduced to below 6 wt. % of water (cf. column 4, lines 3-17). According to the examples, the breaking stress (tensile strength) is not more than 10.0 $N/mm^2$.

U.S. Pat. No. 5,439,953, incorporated by reference, discloses a one-step process for the preparation of polymer-modified starch materials wherein a mixture of starch, an aqueous dispersion of a synthetic polymer and optionally but preferably a plasticizer selected from the group consisting of ethylene glycol, propylene glycol, butane diol, glycerol and ethers thereof are extruded. According to the examples, the polymer-modified starch materials have a tensile strength of not more than 4.0 $N/mm^2$.

According to EP A 298.920 of Warner Lambert Co., the starting material is treated with water and/or acid having a pH of 3 or lower to remove electrolytes and divalent cations so that the processability of the starch during the destructurising step is improved.

GB A 2.190.093 of Warner Lambert Co. discloses a process for the preparation of a destructurised starch granulate wherein a mixture of starch, a texturising agent, preferably titanium oxide, silicon dioxide or a mixture thereof, and a lubricant/release agent and/or a melt-flow accelerator are extruded. This granulate would have good flow behaviour used for the manufacture of shaped articles such as capsules by injection moulding.

EP A 304.401 of Novamont S.p.A. discloses shaped articles made from pre-processed starch and a two-step process for the preparation of destructurised starch. In the first step of this process, a composition comprising starch is extruded at a water content of 10-20 wt. %, based on the weight of the composition, at a temperature of 120° to 190° C., preferably 130° to 190° C., and a pressure within the range of the vapour pressure of water at the prevailing temperature and 15 MPa, preferably 10 MPa, more preferably 8 MPa, to form a starch granulate. This starch granulate has a water content of 10-20 wt. %, preferably 12-19 wt. %, more preferably 14-18 wt. %, based on the weight of the starch granulate. The starch granulate is then again processed in a second step in an extruder at a temperature of 80° to 200° C., preferably 120° to 190°, more preferably 140° to 180° C., and a pressure of 0 to 15 MPa, preferably 0 to 10 MPa, and most preferably 0 to 8 MPa to form a melt. The melt is subsequently transferred to a mould while the water content is kept constant and the shaped articles are then formed by cooling the melt to a temperature below the glass transition temperature of the melt. Instead of the second extrusion step, the shaped article can be manufactured by injection moulding, wherein for the injection step a pressure of 30 to 300 MPa (=30,000,000 to 300,000,000 N/m$^2$=300 to 3000 bar), preferably 70 to 220 MPa, is employed. The shaped articles include bottles, sheets, films, packaging materials, pipes, rods, laminates, sacks, bags and pharmaceutical capsules which indicate that these shaped articles have poor biologically degradability. Tests further revealed that the two-step process according to EP A 304.401 provided shaped articles having higher extensions at break when compared with shaped articles formed in a single-step process as disclosed in e.g. EP A 118.240. Tests further showed that extensions at break of moulded test specimen decreased with increasing moisture content (cf. FIG. 5).

EP A 474.705 of Starch Australia Ltd. discloses a process for the manufacture of films, said films having a good mechanical strength and good stretchability. The films are produced from a granulate made from starch having a high amylose content, preferably at least 50 wt. %, in an extruder equipped with a flat die wherein during the extrusion process water is removed by applying a vacuum. Removal of water is said to be beneficial as it would provide a thermoplastic material unknown from the prior art which is compatible with polymer films and which can be co-extruded with other polymers, e.g. polypropylene. EP A 495.056 of Cerestar Holding B.V. relates to a similar process for making a film wherein "superdry" starch, i.e. starch containing less than 8 wt. % water, is employed. In particular, EP A 495.056 discloses a process for extruding or injection moulding starch containing compositions, said process providing substantially transparent products, provided that the starch used contains less than 8% by weight of water, that the water content of the starch in the barrel of the extruder or injection moulding machine is controlled so it is within the range of 5 to 20% by weight (based on the weight of the starch) and that water is removed from the composition immediately before the composition leaves the barrel of the extruder or the injection moulding machine so that the water content of the composition passing through the die and/or entering the mould is less than 3% by weight of the starch.

EP A 774.975 of Van De Wijdeven discloses that the preparation of fully destructurised starch and the manufacture of shaped articles such as implants that are made of the fully destructurised starch, optionally in the form of a granulate, can be made by processes conducted by the methods disclosed in either EP A 282.451, GB 2.190.093 or EP A 304.401. However, it is preferred that the technique employed comprises an extrusion step followed by an injection moulding step as is disclosed in EP A 304.401 wherein it is of utmost importance that by variation of pressure, temperature, residence time, amount of water and the like a shaped article such as an implant is provided that is not toxic and degradable in vivo to a vertebrate, e.g. a mammal. It is furthermore preferred that a starch essentially free from amylose, e.g. waxy maize starch, is used as starting material for the preparation of the granulate. Example 1 of EP A 774.975 discloses the preparation of a granulate of fully destructurised starch by extruding commercially available, pure native starch, optionally in the presence of biocompatible additives, at a pressure of 15 MPa and 160° C. according to the method disclosed in EP A 282.451 (which employs an inorganic acid as a chain scission catalyst) and EP A 304.401 (which does not employ a chain scission catalyst). Example 2 of EP A 774.975 discloses the manufacture of bullet shaped implants from the granulate as obtained in Example 1, wherein the method according to EP A 282.451 or EP A 304.401 is employed. Consequently, the granulate and the bullet shaped articles according to EP A 774.975 are different from those of the present invention.

EP A 994.654 of Aventis Res. & Tech. & Co. discloses a thermoplastic mixture that can be used to manufacture e.g. hollow solid shaped articles. The thermoplastic mixture comprises starch and a polyhydroxy carboxylic acid derived from an aldose or a ketose as a plasticizer or a lactone of said polyhydroxy carboxylic acids.

The use of starch based compositions for producing other materials and products is well known in the art. For example, film materials and fibres are disclosed in EP A 474.705, EP A 495.056, EP A 560.014, EP A 1.035.163 and EP A 1.103.254. Expanded products based on starch derived materials are for example disclosed in EP A 376.201, EP A 544.234, EP A 712.883 and EP A 1.064.330. However, such expanded products have a relatively low bulk density, e.g. 1.6 to 80 kg/m$^3$ (cf. EP A 376.201) and are often used for packaging applications. The use of mixtures of starch and synthetic polymers for all kind of purposes is also well known in the art. Reference is for example made to EP A 327.505, EP A 413.798, EP A 400.532, EP A 436.698, EP A 437.561, EP A 437.589, EP A 494.287, EP A 539.541, EP A 575.349, EP A 519.367, EP A 522.358, EP A 560.244, EP A 670.683, EP A 679.172, EP A 682.070, EP A 711.326, EP A 775.171, EP A 819.147, EP A 1.282.662 and U.S. Pat. No. 6,821,538. However, products based on such mixtures have inter alia a poor biodegradability and are suspicious regarding (cyto)toxicity and suitability for implantation The biodegradable materials produced by the methods according to the prior art have several disadvantages. For example, many methods employ additives such as plasticizers that are not of natural origin and are undesired in biodegradable materials intended for e.g. human applications. Such additives are in particular undesired as they may give rise to inflammation and other adverse effects such as the formation of granulomas when shaped articles made of these biodegradable materials come in contact with living tissue. Additives such as lubricants and extenders are also commonly used which may cause similar undesired effects. Many methods also employ other sources of starch besides native starch, e.g. (chemically) modified starch, starch derivatives, combinations with hydrophilic (synthetic) polymer compositions (cf. for example EP A 110.824), and the like.

The prior art has also not acknowledged processing factors such as pressure, temperature and residence time, in particular in relation to mechanical properties, (cyto)toxicity properties and in vitro and in vivo degradability of the biodegradable material and of the shaped articles manufactured from the biodegradable material.

SUMMARY OF THE INVENTION

Accordingly, the present invention relates to a biodegradable material comprising about 50 to about 100 wt. % of opened starch or of a mixture of opened starch and destructurised starch, based on the total weight of the biodegradable material, said biodegradable material having a bulk density of 1.0 to 1.5 kg/dm$^3$.

In particular, the term "opened starch" relates to a different physical state of the starch than the term "destructurised starch" as used in the prior art dealing with injection mouldable starch compositions.

The present invention also relates to a process for preparing a biodegradable material and its use for manufacturing shaped articles, in particular shaped articles intended for pharmaceutical, neutraceutical and implantation purposes.

BRIEF DESCRIPTION OF FIG. 1

FIG. 1 shows the number of tension fields per 3.2 cm$^2$ observed in tensile bars specimen made of opened starch as function of the residence time in the extrusion process (at constant water content of the starch and at constant extrusion temperature). The extrusion pressure was fixed at 14 MPa. Data are taken from Tables 4 and 5.

DETAILED DESCRIPTION OF THE INVENTION

Definitions and Expressions

The term "chemically non-modified starch" is to be understood as a native starch material that is obtained from seeds and cereals, e.g. corn, waxy corn, high amylose corn, oats, rye, maize, wheat and rice, or roots, e.g. potato, sweet potato and tapioca. Preferably, the starch material is potato starch, maize starch or corn starch, most preferably potato starch. The term "chemically non-modified starch" also includes physically modified starch materials or mechanically modified starch materials. Physical modification can be achieved by e.g. cooking or gelatinisation whereas mechanical modification can be achieved by dry grinding. However, according to the invention, it is preferred that the starch material is not physically modified. It is further well known that the main components of native starch material are amylose and amylopectine, the molecular weights thereof being dependent from the origin of the starch (cf. for example Kirk-Othmer, Encyclopedia of Chemical Technology, Vol. 22, 699-719, 1997).

The prior art, in particular in EP A 774.975, incorporated by reference herein, discloses "destructurised starch" and "substantially destructurised starch" which implies that essentially all starch particles are destructurised, i.e. all starch granules are disrupted, and within the disrupted starch granules, the starch molecules are dispersed. In this document, the materials "destructurised starch" and "substantially destructurised starch" are indicated by the generic term "destructurised starch" for convenience.

The present invention, however, relates inter alia to "opened" starch which is a materially different product. Opened starch is characterised by a partly disruption of the starch granules, whereby at least a small part of packages of the molecules within the granules retain their original radiary structure, i.e. that: starch granules swell, get opened, may leak amylose but not amylopectin. In opened starch, the amylopectin layers stay at least partly intact, although the hydrogen bonds that were originally present in between the amylopectin layers are broken. Whereas destructurised starch is obtained at relatively high temperatures and/or relatively long residence times and/or high shear and/or low water contents during processing within the extruder and/or injection moulding machine, opened starch is obtained under less harsh, more subtle processing conditions: in general higher water contents, less shear, shorter residence time during processing, lower temperatures, higher pressures, followed by "ripening" of the extrudate.

Opened starch has an increased susceptibility for enzymes which is due to the fact that in opened starch granules the macromolecules can be reached by the proteineous enzymes, whereas in destructurised starch granules enzymes can only reach the macromolecules with great difficulty. This is caused by the fact that opened starch is capable of absorbing aqueous fluids, e.g. water, very rapidly and in high quantities (until fifty times its own weight) whereas substantially destructurised starch hardly absorbs aqueous fluids.

The difference between these materials can for example first be demonstrated by the number of tension fields in shaped articles and test specimen made of destructurised starch and shaped articles and test specimen made from opened starch as will be explained in more detail below. In principle, shaped articles and test specimen made of destructurised starch do hardly show tension fields and these products appear to be less susceptible to enzymatic degradation. In contrast, shaped articles and test specimen made of opened starch show a relatively high number of tension fields and are far more easily degraded by enzymatic action which is advantageous in certain applications, in particular in pharmaceutical, neutraceutical and implantation applications. Secondly, the increased susceptibility for enzymatic action is due to the fact that in opened starch granules the macromolecules (such as the amylopectin layers that are no longer interconnected by hydrogen bonds) can be reached by the proteineous enzymes, whereas in native starch granules enzymes cannot reach the macromolecules, and whereas in essentially (on molecular level) destructurised starch these molecules recrystallise, making the macromolecules unreachable for enzymes. According to the present invention, opened starch is characterized by at least 2, more preferably at least 5, even more preferably at least 10, yet even more preferably at least 25 and most preferably at least 50 tension fields/3.2 cm$^2$ as determined by visual inspection of tensile bars 5 mm wide and 2 mm thick which are made of opened starch using a standard polarised light stereomicroscope. Destructurised starch is therefore characterized by less than 2 tension fields/3.2 cm$^2$, in particular less than 1 tension field/3.2 cm$^2$.

The verb "to comprise" as is used in this description and in the claims and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there is one and only one of the elements. The indefinite article "a" or "an" thus usually means "at least one".

Destructurised Starch

Destructurised starch and processes for making destructurised starch are well known in the art and are for example disclosed in EP A 118.240, EP A 282.451, EP A 298.920, GB A 2.190.093, EP A 304.401, EP A 474.705, EP 495.056, EP A 774.975 and EP A 994.564, all incorporated by reference herein. In these processes, starch, a plasticizer, e.g. water, and optionally other components are extruded under relatively severe conditions, e.g. high pressures and temperatures and long residence times. However, according to the present invention, it is preferred that the destructurised starch is made from starch and a plasticizer, wherein it is preferred that the plasticizer is water. Preferably, the starch is a chemically non-modified starch.

The destructurised starch comprises preferably about 10 to about 25 wt. % of water, preferably about 11 wt. % to about 22 wt. %, more preferably about 12 wt. % to about 20 wt. %, based on the total weight of the destructurised starch.

The degree of destructurisation is dependent from the process conditions and may vary between "slightly destructurised starch" to "substantially fully destructurised starch". Most preferably, the destructurised starch is manufactured by the method disclosed in Example 1 of EP A 774.975.

Opened Starch

Opened starch and processes for making opened starch are, however, unknown in the art. As disclosed above, a very typical and important feature of the material designated opened starch, is that shaped articles made thereof have tension fields. It was surprisingly found that the presence of tension fields is correlated to the in vivo degradation rate of shaped articles made from opened starch according to the invention, the destructurised starch known from the prior art, and from mixtures of opened starch and destructurised starch. Furthermore, the number of tension fields was found to decrease to a negligible number, i.e. almost zero, when only destructurised starch was used. As a consequence, process conditions have been designed that provide a biodegradable material and shaped articles made thereof having excellent properties, in particular with respect of mechanical properties, (cyto)toxicity properties and in vivo degradability. In addition, biodegradability of shaped articles could be tuned by using mixtures of opened starch and destructurised starch.

Tension fields could be made visible in shaped articles and test specimen formed from the opened starch according to the present invention by visual inspection of the shaped articles and the test specimen with the aid of polarised light. The number of tension fields in the shaped articles and test specimen was determined by counting and the counted number correlated well to the biodegradability (in vivo and in vitro) of the shaped article or test specimen. For example, it appeared that if the shaped article is a solid bullet-like article as for example disclosed in EP A 774.975, but made from opened starch according to the present invention, the number of tension fields is far higher than when made from the destructurised starch known from the prior art.

The opened starch preferably comprises about 10 to about 25 wt. % of water, preferably about 11 wt. % to about 22 wt. %, more preferably about 12 wt. % to about 20 wt. %, based on the total weight of the opened starch.

The opened starch according to the present invention is preferably manufactured by a process wherein in a first step a chemically non-modified starch comprising about 15 wt. % to about 50 wt. % water, preferably about 25 wt. % to about 45 wt. % based on the total weight of the chemically non-modified starch, is extruded in the presence of a plasticizer, the plasticizer being water, at a temperature of about 30° to about 150° C., preferably about 50° to about 130° C., more preferably about 60° to about 110° C., and a pressure of about 45 to about 250 bar (about 4.5 to about 25 MPa), preferably about 70 to about 200 bar (about 7 to about 20 MPa), to form a granulate. The amount of plasticizer added is preferably about 20 wt. % to about 50 wt. %, more preferably about 25 wt. % to about 45 wt. %, based on the total weight of chemically non-modified starch and the plasticizer. The residence time of the chemically non-modified starch and the plasticizer in the heating zones of the extruder is preferably about 0.1 to about 7 minutes, more preferably about 0.2 minute to about 5 minutes and most preferably about 0.2 minute to less than about 5 minutes. The relative high water content is advantageous since lower pressures (because in excess of water, the hydrogen bonds between the layers of starch molecules can more easily be loosened without loosing the molecular arrangement within the opened starch granule) and lower shear than normally applied in the manufacturing process of the destructurised starch can be employed.

It is preferred that the weight average molecular weight of the chemically non-modified starch is greater than 20,000,000. More preferably, the weight average molecular weight of the chemically non-modified starch is greater than 20,000,000 up to 200,000,000.

The water content of the opened starch according to the present invention at this stage of the manufacturing process, i.e. the granulate, is preferably about 20 wt. % to about 50 wt. %, more preferably about 25 wt. % to about 45 wt. %, based on the total weight of the opened starch. At this stage of the process, the water content of the opened starch (granulate) is higher when compared with the water content of the chemically non-modified starch used as starting material.

According to the present invention, it is preferred to further subject the granulate to an annealing step or a conditioning step, wherein the water content of the opened starch is reduced to from about 10 to about 25 wt. %, preferably about 13 wt. % to about 19.5 wt. %, more preferably about 15.5 wt. % to about 17.5 wt. %, based on the total weight of the opened starch. This annealing step or conditioning can be performed at a temperature of from about 10° to about 80° C. This annealing step or conditioning step is further preferably performed for a period of about 0.2 to about 48 h, more preferably about 1 to about 3 h, followed by a ripening process of about at least 24 hours at room temperature. The annealing step is beneficial for an evenly distribution of the plasticizer through the opened starch.

Consequently, according to a preferred embodiment of the present invention, the invention relates to a process for preparing an opened starch, wherein:

(a) in a first step a chemically non-modified starch comprising about 15 wt. % to about 50 wt. % water, based on the total weight of the chemically non-modified starch, is extruded in the presence of a plasticizer, the plasticizer being water, at a temperature of about 30° to about 150° C. and a pressure of about 45 to about 250 bar (about 4.5 to about 25 MPa) to form a granulate; and (b) optionally, but preferably, in a second step the granulate is annealed or conditioned, preferably for a period of about 0.2 to about 48 h, to form the opened starch, wherein the water content of the opened starch is about 10 to about 25 wt. % of water, based on the total weight of the opened starch.

Hence, the present invention also relates to an opened starch obtainable by this process.

Like in the process for the preparation of destructurised starch, common additives which are well known in the art may be used in the process for the preparation of opened starch, provided that these additives do not have an adverse effect on mechanical properties, (cyto)toxicity properties and in vivo degradability properties and do not induce undesired adverse side effects such as e.g. inflammations and formation of granulomas. Such common additives include texturising agents, lubricants/release agents, melt flow accelerators and mixtures thereof. An example of a suitable texturising agent is titanium dioxide. Suitable examples of lubricants/release agents are animal fats, vegetable fats or mixtures thereof. Suitable melt flow accelerators are monoglycerides, diglycerides and mixtures thereof, and phosphatides, wherein it is preferred that the monoglycerides and diglycerides are derived from long-chained fatty acids, preferably $C_{14}$, $C_{16}$, $C_{18}$ fatty acids and wherein it is preferred that the phosphatide is a lecithin. When used, it is preferred that the amount of texturising agent is about 0.01% to about 1.0% by weight, preferably 0.02% to about 1.0% by weight, based on the total weight of the chemically non-modified starch and plasticizer. The preferred amount of the lubricant/release agent is about 0.4% to about 5.0% by weight, preferably about 0.8 to about 2.0% by weight, based on the total weight of the chemically non-modified starch and plasticizer. The preferred amount of the melt flow accelerator is about 0.01% to about 5.0% by weight, preferably about 0.05 to about 2.0 by weight, based on the total weight of the chemically non-modified starch and plasticizer.

The opened starch according to the present invention comprises processed amylose and processed amylopectine. The processed amylose and processed amylopectine in the opened starch each can be individually analysed. Compared to amylose and amylopectine of the chemically non-modified starch, the processed amylose and processed amylopectine in the opened starch may have undergone alterations and are therefore indicated by the adjective 'processed'.

The processed amylopectine of the opened starch according to the present invention has preferably a weight average molecular weight of about 20,000,000 to about 100,000,000 as determined by MALLS (Multi Angle Laser Light Scattering) on samples that were obtained after DMSO solubilisation and precipitation in alcohol. By the term "processed" as used in this document regarding the amylose and amylopectine components, it is intended to indicate that these components may be different from the amylose and amylopectine as they occur in the chemically non-modified starch, i.e. that during processing some degradation or modification may have occurred. The molecular weight distribution $M_w/M_n$ of the processed amylose is preferably in the range of about 2 to about 3. The weight average molecular weight of the processed amylose is preferably in the range of about 500,000 to about 2,000,000.

Biodegradable Material

The biodegradable material according to the present invention comprises opened starch or a mixture of opened starch and destructurised starch. Preferably, the biodegradable material according to the present invention comprises 50-100 wt. % of opened starch or of a mixture of opened starch and destructurised starch, more preferably 70-100 wt. %, even more preferably 80-100 wt. %, yet even more preferably 90-100 wt. %, based on the total weight of the biodegradable material. These weight percentages of opened starch and destructurised starch include the water contents mentioned above for opened starch and destructurised starch. The remainder of the biodegradable material, i.e. 0-50 wt. %, preferably 0-30 wt. %, even more preferably 0-20 wt. %, yet even more preferably 0-10 wt. %, based on the total weight of the biodegradable material, comprises other components selected from the group of cellulose, cellulose derivatives and analogues and biodegradable synthetic polymers and copolymers. According to a particularly preferred embodiment of the invention, the biodegradable material consists only of opened starch or a mixture of opened starch and destructurised starch.

According to a preferred embodiment of the present invention, the biodegradable material comprises a mixture of opened starch and destructurised starch, wherein the weight ratio of opened starch to destructurised starch is preferably between 100:0 and 1:99, more preferably between 100:0 and 50:50, even more preferably between 100:0 and 75:25 and most preferably between 100:0 and 80:20, based on the total weight of the biodegradable material. Higher amounts of opened starch are generally preferred when a rapid biodegradation of the biodegradable material is desired and a reduction of risks of adverse side-effects, e.g. inflammations and formation of granulomas, is necessary.

The biodegradable material according to the present invention has further a bulk density of about 1.0 to about 1.5 kg/dm$^3$, preferably about 1.2 to about 1.5 kg/dm$^3$.

The biodegradable material according to the present invention is preferably a granulate which enables easy further processing.

Additionally, the biodegradable material according to the present invention has a tensile strength of at least about 20 N/mm$^2$ as determined with test specimen made from the biodegradable material by injection moulding, wherein the tensile strength was determined on a Zwick testing machine of the type Z 2.5. Obviously, the tensile strength is dependent from the storage conditions, e.g. relative humidity and storage time, of the biodegradable material and of the test specimen. However, evaluation of test specimen of the biodegradable material has shown that tensile strengths up to about 70 N/mm$^2$ can be attained. Consequently, the biodegradable material according to the present invention has a tensile strength of at least about 20 N/mm$^2$ up to about 70 N/mm$^2$.

In certain applications, for example if a relatively slow degradation is necessary as in sustained release and side-effects are considered acceptable, it may be desired that the biodegradable material comprises other components which have been used in the prior art. Such components include materials such as hydroxypropyl cellulose and hydroxyethylcellulose (indicated above as "the remainder of the biodegradable material") and "biodegradable" synthetic polymers or copolymers comprising one or more monomers selected from the group consisting of hydroxyl alkanoates wherein the alkyl group comprises 1 to 12 carbon atoms, lactide, glycolide, ε-caprolactone, 1,4-dioxane-2-one, 1,5-dioxepan-2-one, trimethylene carbonate (1,3-dioxane-2-one) and mixtures thereof, wherein it is generally preferred that the copolymer is a random copolymer or a block copolymer and wherein the block copolymer is preferably a diblock copolymer or a triblock copolymer. Such polymers and copolymers are well known in the art and are for example disclosed in U.S. Pat. Nos. 2,668,162, 2,703,316, 3,636,956, 3,839,297, 4,137,921, 4,157,437, 4,243,775, 4,443,430, 5,076,983, 5,310,865 and 6,025,458, all incorporated by reference herein. As will be apparent to those skilled in the art, the degradation can also be controlled by varying the weight ratio of opened starch and destructurised starch.

The present invention also relates to a process for preparing a biodegradable material, said biodegradable material comprising about 50 to about 100 wt. % of opened starch or of a mixture of opened starch and destructurised starch, based on the total weight of the biodegradable material, said biodegradable material having a bulk density of 1.0 to 1.5 kg/dm$^3$, wherein:

(a) an opened starch is made by extruding a chemically non-modified starch comprising about 15 wt. % to about 50 wt. % water, based on the total weight of the chemically non-modified starch, in the presence of a plasticizer, the plasticizer being water, at a temperature of about 30° to about 150° C. and a pressure of about 4.5 to about 25 MPa to form a granulate, the amount of plasticizer added being about 20 wt. % to about 50 wt. %, based on the total weight of chemically non-modified starch and the plasticizer, and (b) optionally mixing the opened starch with a destructurised starch.

It is preferred that the opened starch and the destructurised starch are mixed with a weight ratio of opened starch to destructurised starch of between 100:0 and 1:99, more preferably between 100:0 and 50:50, even more preferably between 100:0 and 75:25 and most preferably between 100:0 and 80:20, based on the total weight of the biodegradable material.

Shaped Article

The shaped article according to the present invention is preferably manufactured by injection moulding, wherein the biodegradable material according to the present invention is subjected to injection moulding at a pressure of about 500 to about 3000 bar (about 50 to about 300 MPa), preferably about 600 to about 2500 bar (about 60 to about 250 MPa), and a temperature of about 100° to about 200° C., preferably about 150° to about 190° C., with residence times of about 5 seconds to about 300 seconds.

Shaped articles made of opened starch, when solubilised at ambient temperature (i.e. about 15° to about 25° C.) in about 50% in DMSO/water, wherein the ratio DMSO:water is 9:1, preferably have a weight average molecular weight of processed amylopectine of about 5,000,000 to about 25,000,000 as determined by MALLS and weight average molecular weight of processed amylose of about 200,000 to about 1,000,000 as determined by GPC-MALLS-RI. In contrast, the weight average molecular weight of amylose in shaped articles made of destructurised starch is much lower than 200,000, e.g. about 120,000, and the weight average molecular weight of amylopectine in shaped articles made of destructurised starch is much lower than 5,000,000, e.g. about 1,000,000. Consequently, although the injection moulding step reduces the weight average molecular weight of amylose and amylopectine in both opened starch and destructurised starch, the lower values observed in destructurised starch are due to the harsh conditions employed in the preparation of destructurised starch.

The shaped article according to the present invention is in particular suitable for pharmaceutical and neutraceutical purposes and products and for implantation purposes. Preferably, the shaped article is rod-like, capsule-like, bullet-like, needle-like or tablet-like or has a rod-like, bullet-like, capsule-like, bullet-like, needle-like or tablet-like appearance. It is further preferred according to the present invention that the rod-like, bullet-like or needle-like shaped article has a length:diameter ratio of more than 4, more preferably more than 5, provided that the length of the rod-like or shaped article is between 1 mm to 50 mm. The maximum length diameter ratio is dependent of various factors like the weight of the rod-like, bullet-like or needle-like shaped article and the application of the rod-like, bullet-like or needle-like shaped article. However, the upper limit of this ratio is about 500, preferably less than about 100, more preferably less than about 75 and most preferably less than about 50. The length of the rod-like or bullet-like shaped article is preferably 2 mm to 25 mm, more preferably 6 mm to 25 mm.

According to the present invention, it is further preferred that the rod-like, bullet-like or needle-like shaped articles have an inner, hollow portion and have an average wall thickness of about 10 µm to about 2500 µm, preferably about 30 µm to about 1500 µm, more preferably about 50 µm to about 500 µm. Preferably, the rod-like, bullet-like or needle-like shaped articles are provided with a conical tip and a hollow bottom end, although it is obviously possible to provide the hollow rod-like, bullet-like or needle-like shaped articles with a closing means after it is loaded with a substance, for example a biologically active substance as is disclosed in EP A 774.975. In general, hollow rod-like, bullet-like or needle-like shaped articles having an inner, hollow portion are preferred over solid rod-like, bullet-like or needle-like shaped articles.

According to a particular preferred embodiment, the rod-like, bullet-like or needle-like shaped article is used as a kinetic implant, said kinetic implant being made from the biodegradable material according to the present invention, wherein the biodegradable material comprises opened starch or a mixture of opened starch and destructurised starch. In this particular preferred embodiment, the weight ratio of opened starch and destructurised starch in the mixture is preferably between 100:0 and 1:99, more preferably between 100:0 and 50:50, even more preferably between 100:0 and 75:25 and most preferably between 100:0 and 80:20, based on the total weight of the biodegradable material.

Preferably, the biodegradable material comprises 50-100 wt. % of opened starch, or of a mixture of opened starch and destructurised starch, based on the total weight of the biodegradable material. More preferably, the biodegradable material comprises 50-100 wt. % of opened starch or of a mixture of opened starch and destructurised starch, more preferably 70-100 wt. %, even more preferably 80-100 wt. %, yet even more preferably 90-100 wt. %, based on the total weight of the biodegradable material. Most preferably, the biodegradable material consists only of opened starch, in particular when a rapid biodegradation is desired.

The kinetic implant is suitable for the parenteral delivery of biologically active substances. Parenteral delivery includes delivery by injection or infusion which may be intravenous, intraarterial, intramuscular, intracardiac, subcutaneous, intradermal, intrathecal, transdermal, and transmucosal. Preferably, the kinetic implant is used for intramuscular, subcutaneous and transdermal delivery.

The weight of the kinetic implant is preferably such that the kinetic implant can be provided with an amount of kinetic energy in the range of about 0.1 to about 10 J, preferably about 0.2 to about 5 J. This implies that, if the kinetic implant is accelerated to a velocity comparable to the sound velocity (in dry air at about 20° C., the sound velocity is about 340 m/s), the minimum weight is about 1 mg whereas the maximum weight is about 180 mg. However, for human applications, it is in particular preferred that the kinetic energy (based on a velocity of about 340 m/s) of the kinetic implant is in the range of 0.1 to 5 J, preferably 0.1 to 3 J. If higher kinetic energies (based on a velocity of about 340 m/s) are employed, the kinetic implant becomes too awkward for human application. In contrast, kinetic implants as disclosed in U.S. Pat. Nos. 3,982,536 and 3,616,758 which are commercialized by Solid Tech Animal Health, Inc., under the trade name Biobullet® have a kinetic energy (based on a velocity of about 340 m/s) of about 10 to about 50 J (corresponding weight of about 500 to about 2000 milligrams) and are therefore unsuitable for at least human applications.

The kinetic implant according to the present invention has also sufficient strength to enable kinetic delivery, in particular transdermal delivery. Other systems known from the prior art are either too weak and have too less weight (e.g. as disclosed by U.S. Pat. No. 6,811,792) to pass the dermis or are too awkward for use in transdermal applications (e.g Biobullets®). The kinetic implant, as determined by testing solid specimen of the kinetic implant (tensile strength testing was performed with test bars 5 mm wide and 2 mm thick made from the biodegradable material on a Zwick testing machine of the type Z 2.5) have a tensile strength of at least about 20 N/mm² up to about 70 N/mm². Consequently, there are at least four features which determine the suitability of the kinetic implant according to the present invention in parenteral and in particular in transdermal delivery, i.e. (a) length:diameter ratio, (b) length, (c) weight and (d) strength (tensile and bending).

The kinetic implant can be delivered in or to a vertebrate by using a device as for example disclosed in e.g. U.S. Pat. Nos. 5,549,560, 5,989,214 and NL A 9401372, all incorporated by reference.

The shaped article according to the present invention preferably comprises a biologically or pharmaceutically active component. The term "biologically or pharmaceutically active component" includes any substance that has a biological effect or response, e.g. a therapeutic, a prophylactic, a probiotic or an immunising effect, when it is administered to a living organism (in particular a vertebrate) or when a living organism is exposed in some way to the biologically active substance. Consequently, the term "biologically or pharmaceutically active component" includes pharmaceutical agents, therapeutic agents and prophylactic agents. Suitable examples of pharmaceutical agents are antiinflammatory drugs, analgesics, antiarthritic drugs, antispasmodics, antidepressants, antipsychotics, tranquilizers, antianxiety drugs, narcotic antagonists, antiparkinsonism agents, cholinergic agonists, chemotherapeutic drugs, immunosuppressive agents, antiviral agents, antibiotic agents, appetite suppressants, antiemetics, anticholinergics, antihistaminics, antimigraine agents, coronary, cerebral or peripheral vasodilators, hormonal agents, contraceptives, antithrombotic agents, diuretics, antihypertensive agents, cardiovascular drugs and opioids. Suitable examples of therapeutic or prophylactic agents are subcellular compositions, cells, bacteria, viruses, molecules including lipids, organic compounds, proteins and (poly)peptides (synthetic and natural), peptide mimetics, hormones (peptide, steroid and corticosteroid), D and L amino acid polymers, oligosaccharides, polysaccharides, nucleotides, oligonucleotides and nucleic acids, including DNA and RNA, protein nucleic acid hybrids. Suitable examples of proteins and (poly) peptides are enzymes, biopharmaceuticals, growth hormones, growth factors, insulin, monoclonal antibodies, interferons, interleukins and cytokines. Suitable examples of prophylactic agents are immunogens such as vaccines, e.g. live and attenuated viruses, nucleotide vectors encoding antigens, bacteria, antigens. Vaccines may be produced by molecular biology techniques to produce recombinant peptides or fusion proteins containing one or more portions of a protein derived from a pathogen. The biologically active substance may be derived from natural sources or may be made by recombinant or synthetic techniques.

EXAMPLES

Example 1

Shaped articles made by injection moulding of opened starch (made according to the method disclosed in Example 2) were subjected to the following pre-treatment. The shaped articles were first plasticised, where after the samples were subsequently treated with enzymes to hydrolyse α 1→6 glucose bonds and dissolved in DMSO. The solutions contained the amylose and the residue consisted for the major part of amylopectine. The solutions were analysed by using GPC-MALLS-RI (references were standard pullulan samples) for determining amylose content and the $M_n$, $M_w$ and MWD of the amylose. Data are shown in Table 1.

TABLE 1

| Sample No. | Moisture Content (%. wt) | $T^a$ (° C.) | $P^a$ (MPa) | Residence time (seconds)$^a$ | $M_n$ (kg/mol) | $M_w$ (kg/mol) | MWD | Amylose content (wt. %) |
|---|---|---|---|---|---|---|---|---|
| 1. | 19.5 | 160 | 165 | 300 | 289 | 485 | 1.68 | 30.6 |
| 2. | 16.5 | 175 | 200 | 160 | 292 | 501 | 1.72 | 29.6 |
| 3. | 16.5 | 175 | 205 | 80  | 308 | 552 | 1.79 | 26.9 |
| 4. | 16.5 | 190 | 170 | 25  | 243 | 441 | 1.81 | 22.4 |
| 5. | 13   | 190 | 200 | 300 | 100 | 138 | 1.38 | 16.7 |
| 6. | 16.5 | 190 | 140 | 300 | 91  | 115 | 1.27 | 13.3 |

$^a$Injection moulding conditions.

Example 2

Opened starch in granulated form was made according to the following recipe. A chemically non-modified starch (potato starch purchased from Cerestar, molecular weight about 100×10⁶ Dalton) comprising about 14 wt. % of water, based on the total weight of the chemically non-modified starch, was subjected to extrusion in the presence of 0.5% by weight of lecithin (based on the total weight of the chemically non-modified starch and plasticizer) and a plasticizer (water) at an extrusion temperature of 105° and an extrusion pressure of 14 MPa. The total residence time in the heating zones of the extruder was about 150 s. The strands of opened starch leaving the barrel of the extruder were cut to form a granulate. The amount of plasticizer (water) added was 19.5 wt. %, based on the total weight of chemically non-modified starch and the plasticizer. The water content is determined by using a OHaus apparatus, type MB 45 (conditions: 8 min., 105° C.).

Solid rods were made of the opened starch and of the substantially fully destructurised starch as made according to EP A 774.975 and were subjected to a water absorbance test. The solid rods were charged into a beaker and immersed in deionised water. After 10 minutes, the total weight of the rods was determined. The data are shown in Table 2.

TABLE 2

| Material used for making solid rod | Weight (dry) [mg] | Weight (after 10 min.) [mg] | Weight increase (%) |
|---|---|---|---|
| Opened starch | 34.8 | 207.4 | 496 |
| Substantially fully destructurised starch | 33.7 | 42.2 | 25 |

Weight increase was calculated as follows:

100% *{[Weight(after 10 min.)−Weight(dry)]/Weight (dry)}

This example demonstrates that opened starch absorbs water far more rapidly and in much higher amounts when compared to substantially fully destructurised starch according to EP A 774.975. Consequently, upon contact with bodily fluids containing hydrolysing enzymes, opened starch will be degraded much faster than the substantially fully destructurised starch according to EP A 774.975.

Example 3

The step of making test specimen of the opened starch was evaluated with respect to pressure, temperature and moisture content of the chemically non-modified starch. The opened starch was made according the recipe of Example 2. Results are shown in Table 3.

TABLE 3

| Sample No. | Moisture Content (%. wt) | T (° C.) | P (MPa) | Quality |
|---|---|---|---|---|
| 7. | 13 | 160 | 270 | + |
| 8. | 13 | 175 | 270 | ++ |
| 9. | 13 | 190 | 230 | + |
| 10. | 15 | 160 | 260 | + |
| 11. | 15 | 175 | 230 | ++ |
| 12. | 15 | 190 | 190 | + |
| 13. | 18 | 160 | 200 | + |
| 14. | 18 | 175 | 180 | ++ |
| 15. | 18 | 190 | 140 | + |
| 16. | 19.5 | 160 | 180 | + |
| 17. | 19.5 | 175 | 140 | + |
| 18. | 19.5 | 190 | 130 | + |

The quality of the biodegradable material was evaluated by counting the number of tension fields per referenced surface.

Example 4

Tensile strength testing of the opened starch (Example 2) was performed by making tensile bars 5 mm wide and 2 mm thick, and using a Zwick Z 2.5. The results (averages of five measurements) are summarised in Table 4. The pressure during extrusion was 70 bar (7 MPa). The tensile bars were also visually inspected by using a standard polarised light stereomicroscope. The number of tension fields was counted.

TABLE 4

| Sample No. | Moisture Content (%. wt) | T (° C.) | Residence time (s) | Tensile strength N/mm$^2$ | Number of tension fields/3.2 cm$^2$ |
|---|---|---|---|---|---|
| 19. | 13 | 160 | 80 | 53.1 | 123 |
| 20. | 13 | 160 | 160 | 51.4 | 120 |
| 21. | 13 | 160 | 300 | 53.8 | 105 |
| 22. | 13 | 190 | 80 | 57.7 | 50 |
| 23. | 13 | 190 | 160 | 58.2 | 24 |
| 24. | 13 | 190 | 300 | 56.9 | 10 |
| 25. | 15 | 160 | 80 | 48.5 | 105 |
| 26. | 15 | 160 | 300 | 51.1 | 65 |
| 27. | 15 | 190 | 80 | 55.1 | 24 |
| 28. | 19.5 | 160 | 80 | 51.5 | 58 |
| 29. | 19.5 | 175 | 160 | 53.5 | 14 |

The data of Table 4 show that longer residence time slightly increases tensile strength and reduces the number of tension fields. These data also show that higher temperatures result in a higher tensile strength but a lower number of tension fields.

Example 5

Tensile bars (5 mm wide and 2 mm thick) made from opened starch according to the present invention, were visually inspected by using a standard polarised light stereomicroscope. The number of tension fields was counted (area of 3.2 cm$^2$ of the tensile bar). The pressure during extrusion was 70 bar (7 MPa). Data are summarised in Table 5. The data in Table 5 show that longer residence times and higher temperatures reduce the number of tension fields.

TABLE 5

| Sample No. | Moisture Content (%. wt) | T (° C.) | Residence time (s) | Number of tension fields in tensile bars |
|---|---|---|---|---|
| 30. | 15 | 160 | 80 | 105 |
| 31. | 15 | 160 | 160 | 75 |
| 32. | 15 | 160 | 300 | 65 |
| 33. | 15 | 190 | 80 | 24 |
| 34. | 15 | 190 | 160 | 20 |
| 35. | 15 | 190 | 300 | 0 |
| 36. | 19.5 | 160 | 80 | 58 |
| 37. | 19.5 | 160 | 160 | 40 |
| 38. | 19.5 | 160 | 300 | 25 |
| 39. | 19.5 | 190 | 80 | 10 |
| 40. | 19.5 | 190 | 160 | 10 |
| 41. | 19.5 | 190 | 300 | 10 |

Example 6

Solid rods having a length:diameter ratio of about 12 were made from destructurised starch according to EP A 774.975. Prior to the test they were sterilised and degassed over 48 h. Two steam-sterilised glasses of 250 ml were filled with 99 ml of sterile 50 mM phosphate buffered saline (pH 7.5, 0.1 sodium azide). To glass A, a quantity of 1 ml amylase solution (33 U/ml) and to glass B, a quantity of 1 ml 50 mM 50 mM phosphate buffered saline (pH 7.5, 0.1 sodium azide) was added. Before the start of the experiment, an aliquot of 1 ml was taken from both glasses A and B and stored at −80° C. During the test, the sterilised rods were added to glasses A and B and aliquots were collected at regular intervals. The content of amylose in the aliquots was determined by mixing 50 µl of the aliquot with 100 µl demineralised water and 50 µl 2% lugol, followed by photometric determination of the amount of amylase. The results are shown in Table 6, wherein the concentrations are expressed as absorbance values.

In glass A no increase of amylose content is observed, which supports the conclusion that upon the addition of amylase all amylose is degraded at once as soon as the amylose dissolves. In glass B, however, a gradual increase of amylose is observed which can only be due to the gradual dissolution of amylose. Since the contents of glass A mimic the physiological conditions of bodily fluids in a vertebrate, this experiment demonstrates that shaped articles made of destructurised starch according to EP A 774.975 are less suitable for implantation purposes and a rapid release of a biologically or pharmaceutically active agent.

After the test, the test samples were filtered and the residues isolated and dried. The difference between the initial weight of the rod and the weight of the residue is indicative of the amount of degradation. It appeared that in glass A about 50% of the rod was dissolved whereas in glass B this was only about 8%. This in vitro experiment demonstrates that even after 192 h (8 days) still 50% of the rod is detectable. Moreover, in an in vivo experiment wherein solid rods (length about 5 cm, diameter about 4.5 mm, ratio length:diameter about 11) were inserted subcutaneously into a bovine animal it appeared that residual material of the solid rods was still detectable after three weeks.

TABLE 6

| Time (h) | A | B |
| --- | --- | --- |
| 0.00 | 0.024 | 0.025 |
| 0.25 | 0.029 | 0.069 |
| 0.50 | 0.031 | 0.148 |
| 0.75 | 0.043 | 0.166 |
| 1.00 | 0.035 | 0.236 |
| 1.50 | 0.028 | 0.270 |
| 2.50 | 0.083 | 0.320 |
| 4.50 | 0.028 | 0.424 |
| 8.00 | 0.031 | 0.502 |
| 10.50 | 0.088 | 0.522 |
| 22.50 | 0.053 | 0.587 |
| 30.00 | 0.043 | 0.595 |
| 72.00 | 0.043 | 0.560 |
| 120.00 | 0.053 | 0.675 |
| 192.00 | 0.055 | 0.730 |

Example 7

The number of tension fields correlates with the in vivo degradation rate as appears from the following test.

Comparative Sample number 35 (no tension fields; destructurised starch): a solid rod (10 mm length×1 mm diameter, weighing 10 mg) was put in a solution with amylase: after 2 hours, the rod had absorbed some water (about 5 mg), but was still intact, as was a similar rod in a solution without enzyme.

Samples number 30 (105 tension fields; opened starch): solid rods (10 mm length and 1 mm diameter, weighing 10 mg) were put in a solution with amylase: after 2 hours, the complete rods were enzymatically degraded, whereas similar rods in solution without amylase, did absorb much water (about 50 mg, disintegrating into pieces), but did not degrade.

This test shows that products according to the present invention do degrade extremely fast when compared to products made of destructurised starch products.

Example 8

A kinetic implant was made from the biomaterial according to the present invention, wherein the biomaterial consisted of 50 wt % of opened starch and 50 wt. % of destructurised starch and wherein the kinetic implant had a length:diameter ratio of about 12 (length was about 25 mm and the diameter was about 2 mm) and a weight of about 100 mg. The wall thickness was about 100 µm. The kinetic implant was filled with an antigen and was kinetically administered to the neck of pigs from a distance of about 5 mm from the skin. Serum conversion determination established that antibodies were formed thereby demonstrating that the antigen was released.

Example 9

Two solid test specimen (specimen A was made by injection moulding of fully destructurised starch and had a weight of 67.7 mg and a diameter of 1.4 mm; specimen B was made by injection moulding of opened starch and had a weight of 68.5 mg and a diameter of 1.4 mm) were immersed in a vial in 2 ml of a solution containing 2000 IU/ml of α-amylase. This enzyme is only capable of disrupting 1,4-glycosidic bonds. The injection moulding conditions were: temperature of 190° C., pressure of 140 MPa, residence time 300 seconds. The vials were placed in an oven (temperature 37° C.) for 2 h. Subsequently, the vials were removed from the oven, the supernatant was removed and the residue in each vial was dried during 18 minutes at 105° C. The weight of the dried residue of specimen A was 46.3 mg (about 68% of the original weight) whereas the weight of the dried residue of specimen A was 2.1 mg (about 3% of the original weight). Consequently, specimen B was almost completely degraded within 2 h whereas specimen A was degraded for only about 33%. This example also demonstrated that de degradability can be tuned by varying the ratios of opened starch and fully destructurised starch.

The invention claimed is:

1. A biodegradable material having a bulk density of 1.0 to 1.5 kg/dm$^3$ and a tensile strength of at least 20 N/mm$^2$ consisting of starch and, optionally, water, wherein about 50 to 100 wt. % of the starch has at least 2 tension fields/3.2 cm$^2$.

2. The biodegradable material according to claim 1, wherein the starch having at least 2 tension fields/3.2 cm$^2$ has a water content of 10.0 to 25.0 wt. %, based on the total weight of the starch having at least 2 tension fields/3.2 cm$^2$.

3. The biodegradable material according to claim 1, wherein the starch comprises processed amylopectine having a weight average molecular weight in the range of about 20,000,000 g/mol to about 100,000,000 g/mol.

4. The biodegradable material according to claim 1, wherein the starch comprises processed amylose having a molecular weight distribution $M_w/M_n$ in the range of about 2 to about 3.

5. The biodegradable material according to claim 1, wherein the starch comprises processed amylose having a weight average molecular weight in the range of about 500,000 g/mol to about 2,000,000 g/mol.

6. A process for preparing a biodegradable material having a bulk density of 1.0 to 1.5 kg/dm$^3$ and a tensile strength of at least 20 N/mm$^2$ consisting of starch and, optionally, water, wherein about 50 to 100 wt. % of the starch has at least 2 tension fields/3.2 cm$^2$, the process comprising:
(a) extruding a chemically non-modified starch comprising about 15 wt. % to about 50 wt. % water, based on the total weight of the chemically non-modified starch, in the presence of water as a plasticizer, at a temperature of about 30° to about 150° C. and a pressure of about 4.5 to about 25 MPa to form a granulate, wherein the water is in an amount ranging from about 20 wt. % to about 50 wt. %, based on the total weight of chemically non-modified starch and the plasticizer.

7. The process according to claim 6, wherein the chemically non-modified starch and the plasticizer have a residence time in a heating zone of the extruder of about 0.1 to about 7 minutes.

8. The process according to claim 6, further comprising annealing or conditioning of the granulate.

9. The process according to claim 7, further comprising annealing or conditioning of the granulate.

10. The process according to claim 8, wherein the annealing or conditioning is conducted for a period of about 1 to about 48 h.

11. The process according to claim 9, wherein the annealing or conditioning is conducted for a period of about 1 to about 48 h.

12. The process according to claim 6, wherein the chemically non-modified starch has a weight average molecular weight of greater than 20,000,000 g/mol.

13. The process according to claim 6, wherein the starch comprises processed amylopectine having a weight average molecular weight in the range of 20,000,000 g/mol to 100,000,000 g/mol.

14. The process according to claim 6, wherein the starch comprises processed amylose having a molecular weight distribution $M_w/M_n$ in the range of about 2 to about 3.

15. The process according to claim 6, wherein the starch comprises processed amylose having a weight average molecular weight in the range of 500,000 g/mol to 2,000,000 g/mol.

16. A biodegradable material obtained by the process according to claim 6.

17. A process for manufacturing shaped articles comprising subjecting to injection moulding at a pressure of about 7 to about 300 MPa and a temperature of about 100° to about 200° C. a biodegradable material having a bulk density of 1.0 to 1.5 kg/dm$^3$ and a tensile strength of at least 20 N/mm$^2$ consisting of starch and, optionally, water, wherein about 50 to 100 wt. % of the starch has at least 2 tension fields/3.2 cm$^2$.

18. The process according to claim 17, wherein the injection moulding has a residence time is about 5 seconds to about 300 seconds.

19. The process according to claim 17, wherein the shaped article is a rod, bullet, capsule, needle or tablet.

20. The process according to claim 18, wherein the shaped article is rod, bullet, capsule, needle or tablet.

21. A shaped article having a rod, a bullet, a capsule, needle or tablet appearance, the shaped article comprising the biodegradable material according to claim 1.

22. The shaped article according to claim 21, wherein the shaped article has a length:diameter ratio of more than 4, provided that the length of the rod or shaped article is between 1 mm to 50 mm.

23. The shaped article according to claim 21, wherein the shaped article is a hollow shaped article.

24. The shaped article according to claim 22, wherein the shaped article is a hollow shaped article.

25. The shaped article according to claim 23, wherein the shaped article has an average wall thickness of 10 μm to 2500 μm.

26. The shaped article according to claim 24, wherein the shaped article has an average wall thickness of 10 μm to 2500 μm.

27. The shaped article according to claim 21, further comprising a biologically or pharmaceutically active component.

28. The shaped article according to claim 21, wherein the shaped article, having a width of about 5 mm and a thickness of about 2 mm, has a tensile strength of at least about 20 N/mm$^2$ up to about 70 N/mm$^2$.

\* \* \* \* \*